(12) United States Patent
Abe

(10) Patent No.: US 7,999,845 B2
(45) Date of Patent: Aug. 16, 2011

(54) ELECTRONIC ENDOSCOPE SYSTEM

(75) Inventor: Kazunori Abe, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 1335 days.

(21) Appl. No.: 11/529,529

(22) Filed: Sep. 29, 2006

(65) Prior Publication Data
US 2007/0070195 A1    Mar. 29, 2007

(30) Foreign Application Priority Data

Sep. 29, 2005    (JP) ................. 2005-283495

(51) Int. Cl.
*H04N 7/18*    (2006.01)
*A61B 1/04*    (2006.01)

(52) U.S. Cl. .......................... 348/74; 600/101
(58) Field of Classification Search ............ 348/45, 348/72, 77, 65; 600/101
See application file for complete search history.

(56) References Cited

U.S. PATENT DOCUMENTS
2001/0015754 A1    8/2001    Nakashima et al.
2004/0196364 A1    10/2004   Takahashi FOREIGN PATENT DOCUMENTS
| JP | 60-048011 A | 3/1985 |
| JP | 1-251886 A | 10/1989 |
| JP | 5-260479 A | 10/1993 |
| JP | 2001-046334 A | 2/2001 |
| JP | 2001-231739 A | 8/2001 |

OTHER PUBLICATIONS

European Search Report dated Oct. 13, 2010 issued for European Application No. 06020411.2.
Japanse Office Action (with English translation dated Mar. 31, 2011 issued in corresponding Japanese patent application No. 2005-283495.

*Primary Examiner* — Y. Lee
*Assistant Examiner* — Tracy Li
(74) *Attorney, Agent, or Firm* — Birch, Stewart, Kolasch & Birch, LLP

(57) ABSTRACT

In an electronic endoscope system, an RF signal is produced through quadrature modulation of a picture signal that is representative of an image taken through an electronic endoscope. When control signals are entered by an operator through a control section of the electronic endoscope, a data superimposing section superimposes the entered control signals on the RF signal in horizontal scanning intervals within a vertical blanking interval. The RF signal having the control signals superimposed thereon is sent as an electric wave of a single frequency band to a processor. In the processor, a data analyzer carries out sampling to extract the entered control signals if they are superimposed on the picture signal, and analyzes the contents of the entered control signals. Based on the results of analysis, a CPU controls respective components of the signal processor.

4 Claims, 5 Drawing Sheets

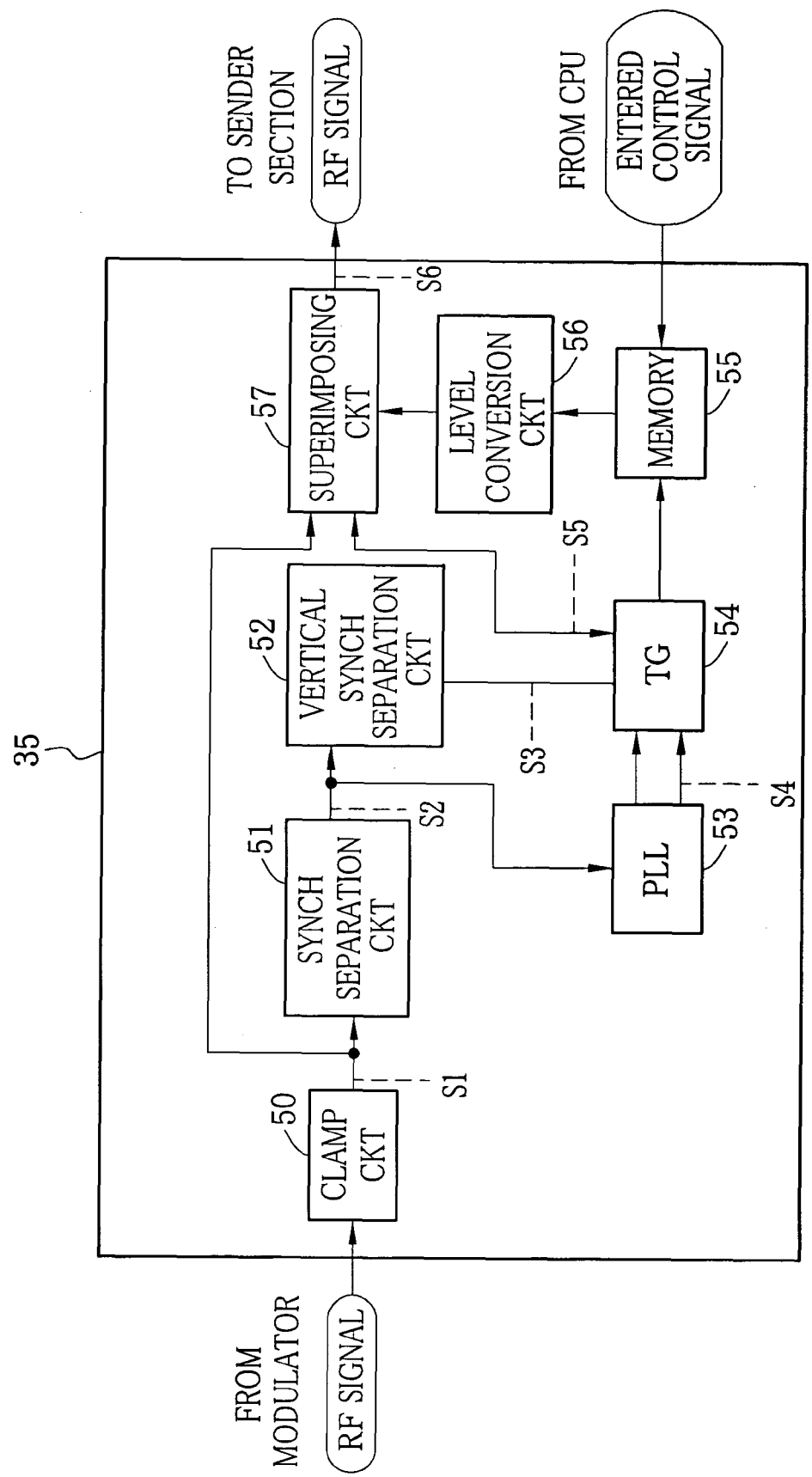

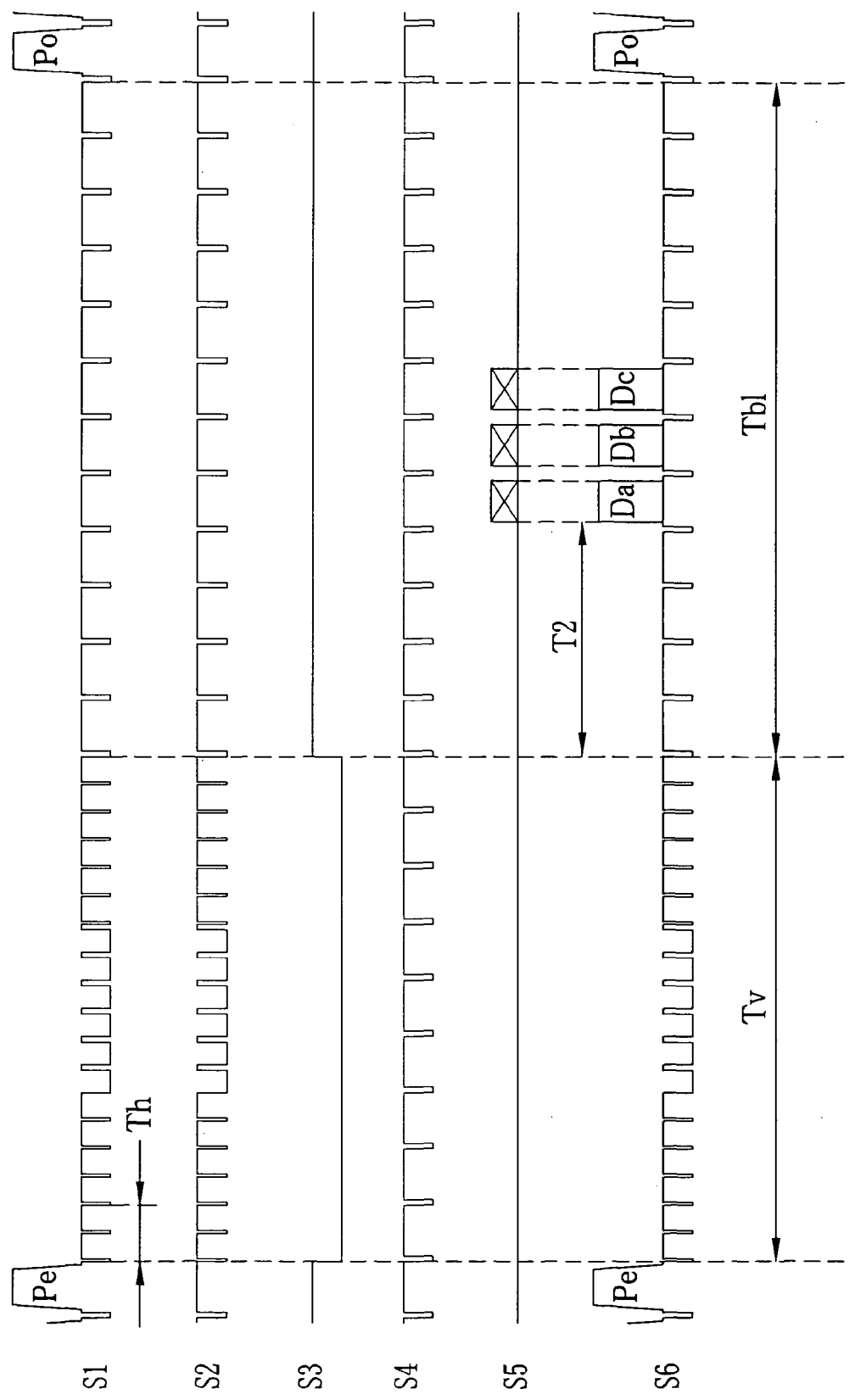

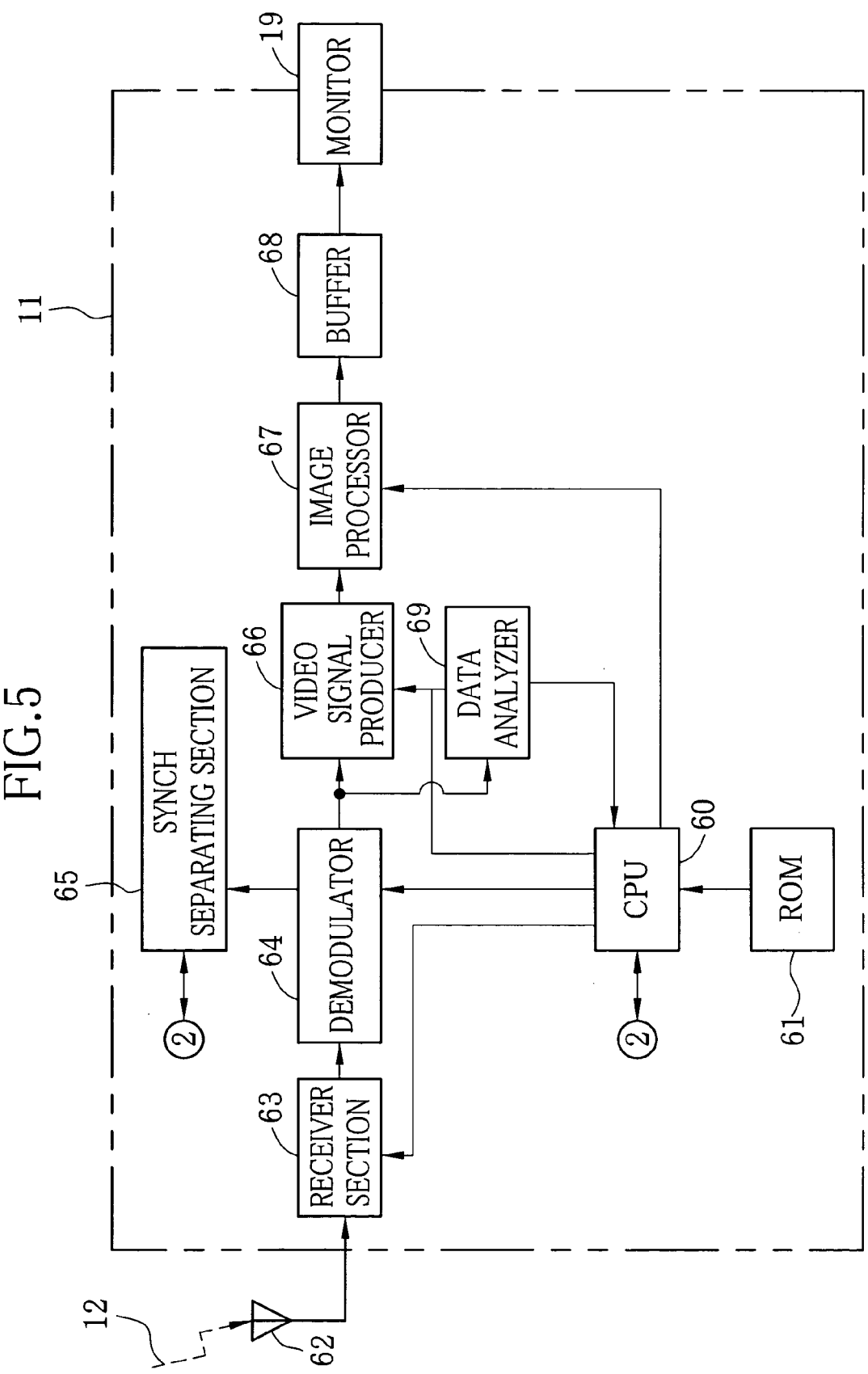

ELECTRONIC ENDOSCOPE SYSTEM

FIELD OF THE INVENTION

The present invention relates to an electronic endoscope system consisting of an electronic endoscope and a processor, which communicate signals to each other using electric waves.

BACKGROUND OF THE INVENTION

Medical diagnoses utilizing an electronic endoscope have widely been practiced in the medical field these days. The electronic endoscope has an imaging device like a CCD, which is built in an end of an elongated probing portion that is introduced into a body cavity, so that the CCD takes an image signal from an internal body site. The image signal is processed in a processor, to display an image of the internal body site, called an endoscopic image, on a monitor.

The electronic endoscope and the processor are usually connected to each other through a signal cable. Also, wireless electronic endoscopes systems have been suggested, for example, in Japanese Laid-open Patent Application Nos. Sho 60-48011 and 2001-046334. In the wireless electronic endoscope system, the electronic endoscope is provided with a modulator and a sender for sending the modulated signal as an electric wave, whereas the processor is provided with a receiver for receiving the electric wave and a demodulator for demodulating the modulated signal. Because the signal is communicated by way of the electric wave, the signal cable is unnecessary, so the handling of the wireless electronic endoscope is superior to those using the signal cable.

In addition to the above-mentioned advantage that the signal cable does not give limit to the handling of the electronic endoscope, and thus the workability is improved, the wireless electronic endoscope system has another advantage. Since there is not any electric connection between the electronic endoscope and the processor, it is unnecessary to maintain a high dielectric strength voltage of about 4 kV between a patient circuit and a secondary circuit, while such a high dielectric strength voltage is necessary for the conventional electronic endoscope system using the signal cable.

The electronic endoscope is also provided with many kinds of control switches, including a freeze switch for capturing a still image from an endoscopic image, and a movie-recording switch for recording motion pictures of the body site.

In the conventional wireless electronic endoscope, control signals entered through the control switches are sent to the processor using an electric wave of a different frequency band from the electric wave for sending the endoscopic image. In practice, it is usual to install a number of electronic endoscope systems together in a specific treatment room in a hospital. Therefore, if an individual electronic endoscope system occupies many working frequency bands, interference can occur between the equipments. To avoid the interference, the number of systems allowed to install in the same room is limited.

SUMMARY OF THE INVENTION

In view of the foregoing, a primary object of the present invention is to provide a wireless electronic endoscope system whose occupied frequency bandwidth is reduced to the minimum, so it permits installing a larger number of these systems in the same place.

To achieve the above and other objects, in an electronic endoscope system of the present invention, which comprises an electronic endoscope having an imaging device for obtaining an image signal from a site to observe inside a body cavity, and a processor for producing an image of the site to observe based on an electric wave received from the electronic endoscope, the electronic endoscope comprises a modulator for producing a radio frequency signal through quadrature modulation of a picture signal that is obtained by digitalizing the image signal; a control section manually operated to enter control signals; a data superimposing device for superimposing the entered control signals on the radio frequency signal in horizontal scanning intervals within a vertical blanking interval of the radio frequency signal; and a sender for sending the radio frequency signal as the electric wave to the processor, after the control signals are superimposed on the radio frequency signal; and the processor comprises a receiver for receiving the radio frequency signal as the electric wave from the electronic endoscope; a demodulator for demodulating the radio frequency signal into the picture signal; a data analyzer for sampling the entered control signals if they are superimposed on the radio frequency signal, and analyzing contents of the entered control signals; and a controller for controlling corresponding components based on results of analysis by the data analyzer.

According to a preferred embodiment, the data superimposing device superimposes the entered control signal at a predetermined time interval from the start of the vertical blanking interval, whereas the data analyzer carries out the sampling only when it detects the predetermined time interval.

Since the control signals entered through the control section are superimposed on the picture signal, and are sent together to the processor as the electric wave of the same frequency band, the electronic endoscope system of the present invention needs to occupy a single channel of frequency band. Consequently, it is possible to raise the number of endoscope systems installable in the same place without the risk of interference between the systems.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 3 is a block diagram illustrating an internal structure of a data superimposing section;

FIG. 4 is a timing chart illustrating wave forms of signals output from respective components of the data superimposing section; and FIG. 5 is a block diagram illustrating an internal structure of the processor.

DESCRIPTION OF THE PREFERRED EMBODIMENTS

Figure 1:
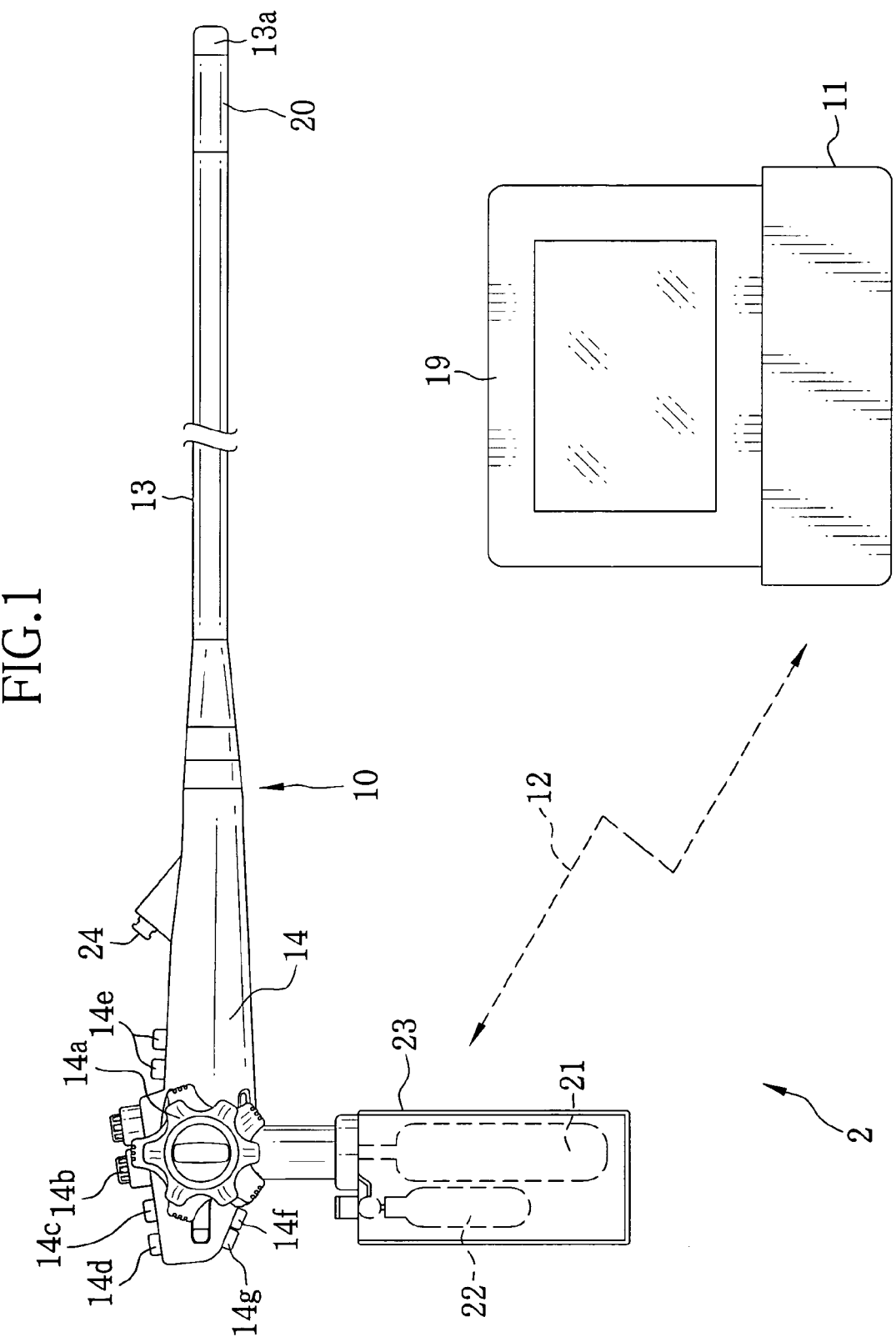
FIG. 1 is a schematic diagram illustrating an electronic endoscope system consisting of an electronic endoscope and a processor.

FIG. 1 shows a wireless electronic endoscope system 2, which consists of an electronic endoscope 10 and a processor 11, which communicates signals to each other by way of electric wave 12.

The electronic endoscope 10 is provided with a probing portion 13 that is introduced into a body cavity, and a control section 14 that is joined to a base end of the probing section 13. Built in a tip portion 13a, which is joined to a distal end of the probing section 13, are an objective lens 15 for forming an optical image of an internal body part to be observed, a CCD 16 as an imaging device for capturing the optical image of the internal body part, an illuminative lens 17, and an LED light source 18 for illuminating the body cavity, see FIG. 2. The image captured through the CCD 16 is sent to the processor 11, and is displayed as an endoscopic image on a monitor 19 that is connected to the processor 11.

Behind the tip portion 13a is provided a curving section 20 consisting of a number of linked curving segments. By operating an angle knob 14a on the control section 14, a number of wires, which are not shown but extend in the probing section 13, are pulled and pushed to curve the curving section 20 appropriately, thereby to direct the tip portion 13a to an aimed point inside the body cavity.

A cartridge 23, in which a water tank 21 containing water and an air cylinder 22 containing air are built, is detachably attached to a bottom position of the control section 14. In cooperation with an action on a watering/airing switch 14b of the control section 14, the water contained in the water tank 21 and the air contained in the air cylinder are fed through a water pipe and an air pipe and ejected from a wash nozzle toward the objective lens 15, though the water pipe and the air pipe are not shown but disposed in the electronic endoscope 10, and the wash nozzle is not shown but formed through the tip portion 13a. Thereby, dirt on the surface of the objective lens 15 is washed away, and the air is sent to the body cavity. The cartridge 23 is so positioned that the wrist of the operator is held on the cartridge 23 to stabilize the electronic endoscope 10 on operating it. Designated by 24 is an inlet for inserting a treatment tool.

Beside the angle knob 14a and the watering/airing switch 14b, the control section 14 is provided with a freeze switch 14c, a release switch 14d, a zooming switch 14e, a movie recording switch 14f and a print switch 14g. The freeze switch 14c is operated to capture a still image from the endoscopic image. The release switch 14d is operated to record the still image on a not-shown recording medium like a memory card. The zooming switch 14e is operated to change magnification of the endoscopic image. The movie recording switch 14f is operated to record the endoscopic image as moving images in a not-shown movie recorder. The print switch 14f is operated to print out a hard copy of the still image through a not-shown printer.

Figure 2:
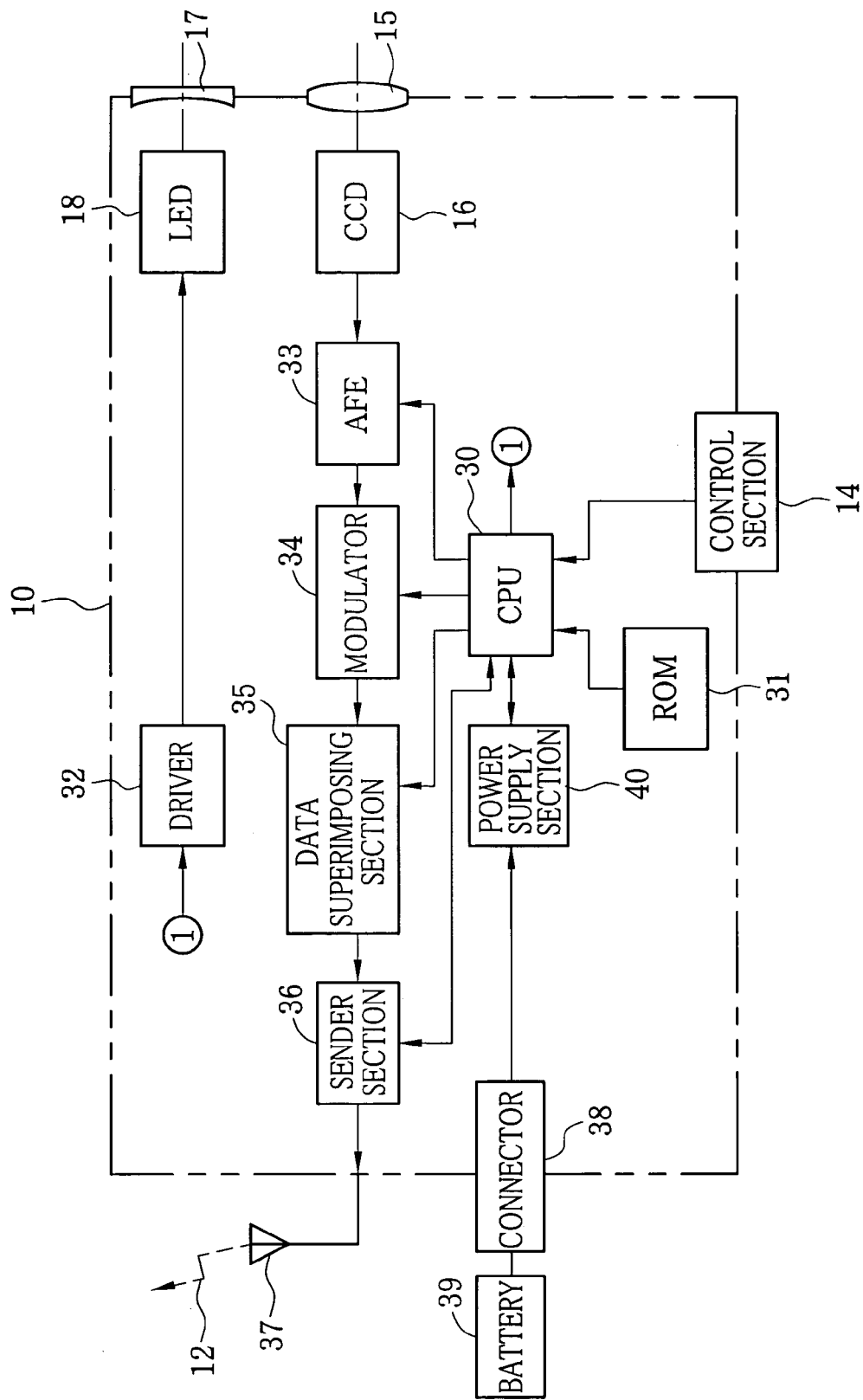
FIG. 2 is a block diagram illustrating an internal structure of the electronic endoscope.

Referring to FIG. 2, the overall operation of the electronic endoscope 10 is under the control of a CPU 30. The control section 14 and a ROM 31 storing various programs and data for controlling the operation of the electronic endoscope 10 are connected to the CPU 30. The CPU 30 reads out necessary program and data from the ROM 31 and writes them on a not-shown RAM that is built in the CPU 30, to control the operation of the electronic endoscope 10 based on the read program and data.

The CPU 30 adds to a control signal, which is entered through one of the switches 14c to 14g of the control section 14, a start code, an end code, a checksum, data of the switch operated to enter the control signal, and data of operational conditions of the switches, such as ON/OFF or continuous pressing of the switches. Thereafter, the CPU 30 outputs the control signal to a data superimposing section 35. Details of the data superimposing section 35 will be described later.

A driver 32 is connected to the LED 18. The driver 32 turns the LED 18 on and off under the control of the CPU 30. The light emitted from the LED 18 is projected through the illuminative lens 17 onto the internal body part to observe. Note that the LED 18 is not necessarily located in the tip portion 13a, but may be located in an intermediate portion inside the control section 14. In that case, the light from the LED 18 is guided through a light guide to the tip portion 13a.

The objective lens 15 forms an optical image of the internal body part on an imaging surface of the CCD 16, so the CCD 16 outputs from individual pixels analog image signals corresponding to the optical image. The analog image signals are fed to an AFE (analog front end) circuit 33, where the analog image signal are subjected to correlated double sampling, and are amplified and converted into a digital picture signal. The digital picture signal is subjected to digital quadrature modulation in a modulator 34, to produce a radio frequency (RF) signal.

In the data superimposing section 35, the entered control signal, as being attached by the various data, is superimposed on the radio frequency signal in a horizontal scanning interval Th within a vertical blanking interval Tb1, as set forth in detail with reference to FIG. 4. As shown in FIG. 3, the data superimposing section 35 is provided with a clamp circuit 50, a synch separation circuit 51, a vertical synch separation circuit 52, a phase locked loop (PLL) 53, a timing generator (TG) 54, a memory 55, a level converter circuit 56 and a superimposing circuit 57.

The clamp circuit 50 is AC-coupled to the modulator 34, to output a signal S1 that reproduces a DC component of the RF signal as produced from the modulator 34. The synch separation circuit 51 eliminates the picture signal components from the signal S1 to output a synchronizing signal S2. The vertical synch separation circuit 52 takes out a vertical synchronizing signal S3 from the synchronizing signal S2, and outputs the signal S3 to the timing generator 54.

The PLL 53 takes out a horizontal synchronizing signal S4 from the synchronizing signal S2, and outputs the signal S4 to the timing generator 54. The PLL 53 also generates a high frequency clock signal to the timing generator 54. The high frequency clock signal is phase-locked at an integral multiple of the horizontal scanning interval, and defines timing of picking up the entered control signals, which are entered through the control section 14, into the memory 55.

Based on the vertical and horizontal synchronizing signals S3 and S4 and the clock signal, the timing generator 54 generates a memory control signal and sends it to the memory 55. The memory control signal defines read-write timing of the entered control signals, and memory addresses of them. The timing generator 54 also generates a superimpose timing signal S6 and sends it to the superimposing circuit 57, for defining timing of superimposing the entered control signal on the radio frequency signal in the superimposing circuit 57.

At the timing defined by the memory control signal from the timing generator 54, the memory 55 reads out the entered control signals, which are entered through the switches 14c to 14g of the control section 14, from the CPU 30, and memorizes the entered control signals. At the same time, the memory 55 outputs the entered control signals to the level conversion circuit 56. The level conversion circuit 56 converts the level of the entered control signals to be suitable for superimposing them on the signal S1 that is output from the clamp circuit 50.

The superimposing circuit 57 superimposes the entered control signals, whose level are converted through the level conversion circuit 56, on the output signal S1 of the clamp circuit 50 at the timing defined by the superimpose timing signal S5 from the timing generator 54, thereby to generate a radio frequency (RF) signal S6. Concretely, the entered control signals are superimposed on the output signal S1 after a predetermined time interval T2 from the start of the vertical blanking interval Tb1. For example, the time interval T2 is four times the horizontal scanning interval Th. Finally, the radio frequency signal S6 is sent as the electric wave 12.

Note that FIG. 4 shows examples of signal wave forms around the vertical blanking interval Tb1 from an end of an even filed to a start of an odd field. Designated by Pe is a horizontal scanning picture signal of the even field, and Po is a horizontal scanning picture signal of the odd field. Tv designates the vertical synchronizing interval. Da, Db and Dc represent the entered control signals as superimposed in the superimposing circuit 57. These signals can include data of at most 20 bits individually.

Referring back to FIG. 2, the sender section 36 sends the radio frequency signal S6 as the electric wave 12 through an antenna 37 to the processor 11. While none of the switches 14c to 14g of the control section 14 is operated, the data superimposing section 35 does not work, so the signal S1 is directly fed to the sender section 36.

The connector 38 is connected to batteries, e.g. serial connected two nickel-hydride batteries having a normal voltage of 1.2V. The electric power from the batteries 39 is supplied through a power supply section 40 to the respective components of the electronic endoscope 10 under the control of the CPU 30. Although it is omitted from the drawings, a battery chamber for containing the batteries 39 is formed behind the control section 14, and the connector 38 is located inside the battery chamber.

FIG. 5 shows the structure of the processor 11, wherein a CPU 60 controls overall operations of the processor 11. The CPU 60 is connected to a ROM 61 that stores various programs and data for controlling the operations of the processor 11. The CPU 60 reads out necessary ones of these programs and data from the ROM 61, writes them on a not-shown built-in RAM, and controls the operation of the processor 11 based on the read program and data.

An antenna 62 receives the electric wave 12 from the electronic endoscope 10. A receiver section 63 amplifies the electric wave 12 as received on the antenna 62, i.e. the radio frequency signal. A demodulator 64 demodulates the original picture signal before being modulated in the electronic endoscope 10, for example, by subjecting the radio frequency signal to digital quadrature detection.

Under the control of the CPU 60, a synch separating section 65 carries out amplitude separation to separate a synchronizing signal from the picture signal as demodulated in the demodulator 64. Thereafter, the synch separating section 65 carries out frequency separation for separating the horizontal synchronizing signal and the vertical synchronizing signal. A video signal producer 66 produces a digital video signal from the picture signal. A image processor 67 treats the video signal, as produced from the video signal producer 66, with various image-processing, such as masking and character data attaching. A buffer 68 temporarily stores the video signal as processed in the image processor 67, and the video signal is used for displaying an endoscopic image on the monitor 19.

A data analyzer 69 executes a sampling process to check if there are any entered control signals superimposed on the picture signal demodulated in the demodulator 64. Specifically, the data analyzer 69 executes the sampling only when it detects the predetermined time interval T2 from the start of the vertical blanking interval Tb1, provided for superimposing the entered control signals.

If there are entered control signals superimposed on the picture signal, the data analyzer 69 takes out the entered control signals from the picture signal to analyze the contents, and sends the results of analysis to the CPU 60. Based on the results of analysis by the data analyzer 69, the CPU 60 controls the operation of the respective components associated with the entered control signals. For example, if the results of analysis show that the freeze switch 14c has been operated, the CPU 60 controls the image processor 67 to stop writing data on the buffer 68. Then, a frozen image is displayed on the monitor 19.

To observe a body cavity with the electronic endoscope system 2, first the LED light source 18 is turned on, and the probing section 13 is introduced into the body cavity, to take endoscopic images through the CCD 16 while illuminating the inside of the body cavity. The taken endoscopic images are observable on the monitor 19.

Concretely, an optical image of a body part inside the body cavity is formed on the imaging surface of the CCD 16 through the objective lens 15, so the CCD 16 outputs image signals corresponding to the optical image. The analog image signals are subjected to correlated-double-sampling, and are amplified and converted into a digital picture signal at the AFE 33.

The modulator 34 subjects the digital picture signal to digital quadrature modulation, to produce a radio frequency (RF) signal. The radio frequency signal is amplified at the sender section 36, and then sent as the electric wave 12 from the antenna 37.

On the other hand, the electric wave 12 from the antenna 37 is received at the antenna 62 of the processor 11, and is amplified as the radio frequency signal in the receiver section 63. The demodulator 64 subjects the amplified radio frequency signal to digital quadrature detection, to demodulate the original picture signal before being modulated in the electronic endoscope 10.

The demodulated picture signal is subjected to synch separation processes in the synch separating section 65 under the control of the CPU 60. The video signal producer 66 produces a digital video signal from the picture signal. The video signal is subjected to various image-processing in the image processor 67. The processed vide signal is stored temporarily in the buffer 68, and is displayed as the endoscopic images on the monitor 19.

Next, a processing sequence executed in response to the operation on one of the switches 14c to 14g of the control section 14 will be described.

When one of the switches 14c to 14g is operated, a corresponding control signal is entered. Then, the CPU 30 adds to the entered control signal a start code, an end code, a checksum, data showing what kind of switch is operated, data showing the switching conditions of the operated switch. The entered control signal with the additional codes and data is sent the data superimposing section 35.

In the data superimposing section 35, the clamp circuit 34 reproduces the DC component of the picture signal as modulated at the modulator 34, and outputs the DC component as the signal S1. The synch separation circuit 51 eliminates the picture signal components from the signal S1 to output the synchronizing signal S2. The vertical synch separation circuit 52 takes out the vertical synchronizing signal S3 from the synchronizing signal S2, and outputs the signal S3 to the timing generator 54.

The PLL 53 takes out the horizontal synchronizing signal S4 from the synchronizing signal S2, and outputs the signal S4 to the timing generator 54. The PLL 53 also generates the high frequency clock signal, which is phase-locked at an integral multiple of the horizontal scanning interval, and defines timing of picking up the entered control signals into the memory 55. The high frequency clock signal is output to the timing generator 54.

Based on the vertical and horizontal synchronizing signals S3 and S4 and the clock signal, the timing generator 54 generates the memory control signal for controlling the memory 55 and the superimpose timing signal S6 for controlling the superimposing circuit 57, and sends them to the memory 55 and the superimposing circuit 57, respectively.

The entered control signal, to which the CPU 30 attaches the additional data, is read in the memory 55 at the timing defined by the memory control signal, and is output to the level conversion circuit 56. The level conversion circuit 56 converts the level of the entered control signal to be suitable for superimposing it on the signal S1 that is output from the clamp circuit 50.

The level conversion circuit 56 outputs the entered control signal to the superimposing circuit 57, so the superimposing circuit 57 superimposes the entered control signal on the output signal S1 of the clamp circuit 50, at the timing defined by the superimpose timing signal S5 that is generated from the timing generator 54, i.e., at the predetermined time interval T2 from the start of the vertical blanking interval Tb1. The subsequent radio frequency signal S6 is fed to the sender section 36, and is sent as the electric wave 12 from the antenna 37 to the processor 11.

When the radio frequency signal S6 is received on the receiver section 63, and is demodulated into the picture signal in the demodulator 64, the data analyzer 69 takes out the entered control signal from the picture signal, analyzes the contents of the entered control signal, and outputs the results of analysis to the CPU 60. Based on the results of analysis, the CPU 60 controls the operations of the respective components corresponding to the entered control signals. Thus, both the picture signal for reproducing the endoscopic image and the control signals entered through the switches 14c to 14g of the control section 14 are sent to the processor 11 on the electric wave 12 of the same frequency band. So the electronic endoscope system of the present invention occupies a single channel of a frequency bandwidth. Consequently, it is possible to raise the number of endoscope systems installable in the same place.

Furthermore, since the data superimposing section 35 superimposes the entered control signals on the radio frequency signal, which is produced by quadrature modulation of the picture signal, at the predetermined time interval T2 from the start of the vertical blanking interval Tb1, the data analyzer 69 can carry out the sampling process for checking if any entered control signals are superimposed on the picture signal, only when it detects the predetermined time interval T2. So the processing time is saved in the data analyzer 69.

Although the present invention has been described with respect to the preferred embodiment having the data superimposing section 35, the present invention is not to be limited to the above embodiment. On the contrary, various modifications will be possible without departing from the scope of claims appended hereto.

What is claimed is:

1. An electronic endoscope system comprising an electronic endoscope having an imaging device for obtaining an image signal from a site to observe inside a body cavity, and a processor for producing an image of the site to observe based on an electric wave received from said electronic endoscope, wherein said electronic endoscope comprises:

a modulator for producing a radio frequency signal through quadrature modulation of a picture signal that is obtained by digitalizing the image signal;

a control section manually operated to enter control signals;

a data superimposing device for superimposing the entered control signals on the radio frequency signal in horizontal scanning intervals within a vertical blanking interval of the radio frequency signal; and a sender for sending the radio frequency signal as the electric wave to said processor, after the control signals are superimposed on the radio frequency signal; and wherein said processor comprises:

a receiver for receiving the radio frequency signal as the electric wave from said electronic endoscope;

a demodulator for demodulating the radio frequency signal into the picture signal;

a data analyzer for sampling the entered control signals if they are superimposed on the radio frequency signal, and analyzing contents of the entered control signals; and a controller for controlling corresponding components based on results of analysis by said data analyzer.

2. An electronic endoscope system as claimed in claim 1, wherein said data superimposing device superimposes the entered control signal at a predetermined time interval from the start of the vertical blanking interval, whereas said data analyzer carries out the sampling only when it detects the predetermined time interval.

3. An electronic endoscope system as claimed in claim 1, wherein said control section comprises at least one of a freeze switch, a release switch, a zooming switch, a movie recording switch and a print switch, wherein said freeze switch is operated to capture a still image of the site to observe, said release switch is operated to record the still image, said zooming switch is operated to change magnification of the image of the site to observe, said movie recording switch is operated to record moving images of the site to observe, and said print switch is operated to print out a hard copy of an image of the site to observe.

4. An electronic endoscope system as claimed in claim 1, wherein said data superimposing device comprises a clamp circuit for reproducing a DC component of the picture signal, a synch separation circuit for separating a synchronizing signal from the picture signal, a vertical synch separation circuit for separating a vertical synchronizing signal from the synchronizing signal, a phase locked loop circuit for separating a horizontal synchronizing signal from the synchronizing signal and generating a high frequency clock signal that is phase-locked at an integral multiple of the horizontal scanning interval, a memory for reading writing the entered control signals, a level conversion circuit for converting the level of the entered control signals, a superimposing circuit connected to an output of said clamp circuit and an output of said level conversion circuit, for superimposing the entered control signal on the picture signal, and a timing generator for generating based on the vertical and horizontal synchronizing signals and the high frequency clock signal a memory control signal for said memory and a superimpose timing signal for said superimposing circuit.

* * * * *